(12) United States Patent
Gould et al.

(10) Patent No.: US 12,694,962 B2
(45) Date of Patent: Jul. 28, 2026

(54) METHOD TO MITIGATE ALLERGEN SYMPTOMS IN A PERSONALIZED AND HYPERLOCAL MANNER

(71) Applicant: Kenvue Brands LLC, Summit, NJ (US)

(72) Inventors: Russell Gould, Yardley, PA (US); Russel Walters, Skillman, NJ (US); Matthew Machado, Skillman, NJ (US); Thomas Shyr, Skillman, NJ (US); Christina I. Lee, Skillman, NJ (US); Jennifer Callaghan, Skillman, NJ (US); Jessica L. Lienert, Fort Washington, PA (US); Grant David Hou, Skillman, NJ (US)

(73) Assignee: Kenvue Brands LLC, Summit, NJ (US)

( * ) Notice: Subject to any disclaimer, the term of this patent is extended or adjusted under 35 U.S.C. 154(b) by 0 days.

(21) Appl. No.: 18/664,900

(22) Filed: May 15, 2024

(65) Prior Publication Data

US 2024/0304293 A1     Sep. 12, 2024

Related U.S. Application Data

(62) Division of application No. 17/031,474, filed on Sep. 24, 2020, now Pat. No. 12,020,792.

(Continued)

(51) Int. Cl.
| | |
|---|---|
| *G16H 20/10* | (2018.01) |
| *G01D 21/00* | (2006.01) |
| *G06N 20/00* | (2019.01) |
| *G16H 10/60* | (2018.01) |

| | |
|---|---|
| *G16H 50/20* | (2018.01) |
| *G16H 50/50* | (2018.01) |
| (Continued) | |

(52) U.S. Cl.
CPC ............. *G16H 20/10* (2018.01); *G01D 21/00* (2013.01); *G06N 20/00* (2019.01); *G16H 10/60* (2018.01); *G16H 50/20* (2018.01); *G16H 50/50* (2018.01); *G16H 50/70* (2018.01); *A61B 5/411* (2013.01)

(58) Field of Classification Search
None
See application file for complete search history.

(56) References Cited

U.S. PATENT DOCUMENTS

| | | |
|---|---|---|
| RE39,871 E | 10/2007 | Skardon |
| 10,255,412 B2 | 4/2019 | Hogg et al. |
| (Continued) | | |

FOREIGN PATENT DOCUMENTS

| | | | | |
|---|---|---|---|---|
| CN | 119028609 A | * | 11/2024 | ............. G06N 20/00 |
| WO | WO 2017106662 A1 | | 6/2017 | |
| WO | WO2019102324 A1 | | 5/2019 | |

OTHER PUBLICATIONS

Richard Warrington, et al.; "Drug allergy", Allergy, Asthma & Clinical Immunology, vol. 14, No. S2, Sep. 1, 2018—p. 60.

(Continued)

*Primary Examiner* — Robert A Sorey

(57) ABSTRACT

A system and method of determining an allergy impact profile of an individual are disclosed. The system and method may be employed to predict allergy impact environmental conditions may have on allergy symptoms of an individual and to recommend treatment of the individual in response to the predicted allergy impact.

1 Claim, 17 Drawing Sheets

Related U.S. Application Data

(60) Provisional application No. 62/904,834, filed on Sep. 24, 2019.

(51) Int. Cl.
*G16H 50/70* (2018.01)
*A61B 5/00* (2006.01)

(56) References Cited

U.S. PATENT DOCUMENTS

| | | | | |
|---|---|---|---|---|
| 10,726,954 | B2 | 7/2020 | Su et al. | |
| 2002/0119769 | A1* | 8/2002 | Heinonen | G01W 1/04 |
| | | | | 455/423 |
| 2007/0004969 | A1* | 1/2007 | Kong | A61B 5/0205 |
| | | | | 128/920 |
| 2014/0114677 | A1 | 4/2014 | Holmes | |
| 2016/0328537 | A1 | 11/2016 | Narula et al. | |
| 2017/0038088 | A1 | 2/2017 | Korber et al. | |
| 2017/0109493 | A1 | 4/2017 | Hogg et al. | |
| 2018/0103889 | A1 | 4/2018 | Tzvieli et al. | |
| 2018/0114592 | A1* | 4/2018 | Apte | G16B 20/40 |
| 2018/0266933 | A1 | 9/2018 | Tamraz | |
| 2018/0292221 | A1* | 10/2018 | Bastide | G06N 5/022 |
| 2019/0108912 | A1* | 4/2019 | Spurlock, III | A61P 25/28 |
| 2019/0156925 | A1* | 5/2019 | Martinez-Arocho | |
| | | | | G16H 15/00 |
| 2019/0156959 | A1 | 5/2019 | Muzio | |
| 2019/0180857 | A1 | 6/2019 | Van Orden | |
| 2019/0189258 | A1 | 6/2019 | Barrett et al. | |
| 2020/0381095 | A1 | 12/2020 | Li | |

OTHER PUBLICATIONS

A. Gonzalez-Quintela, et al.; "Association of alcohol consumption with total serum immunoglobulin E levels and allergic sensitization in an adult population-based survey", Clin. Exp. Allergy, Jan. 1, 2003, pp. 199-205.

International Search Report, PCT/IB2020/058955, dated Dec. 9, 2020.

* cited by examiner

Figure 1
PRIOR ART
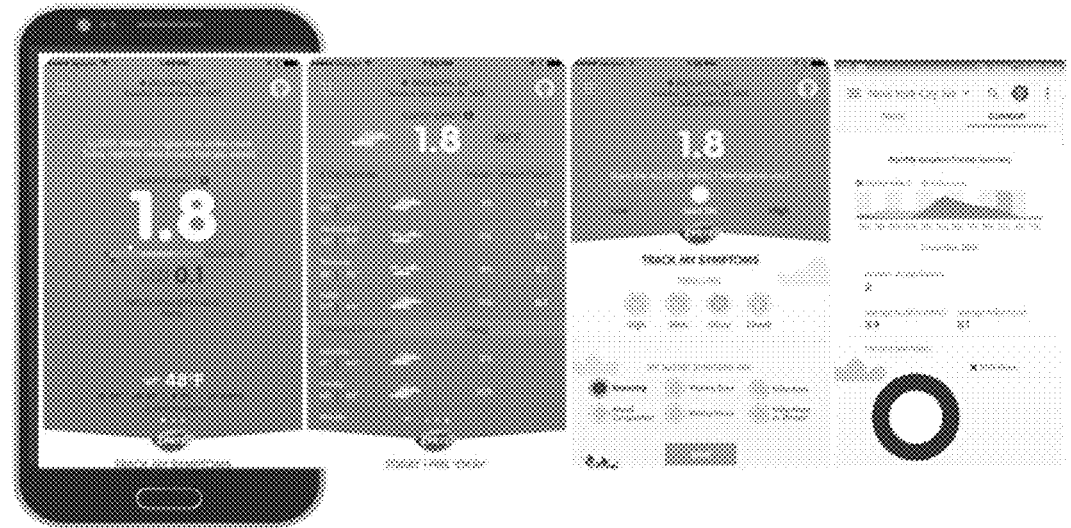
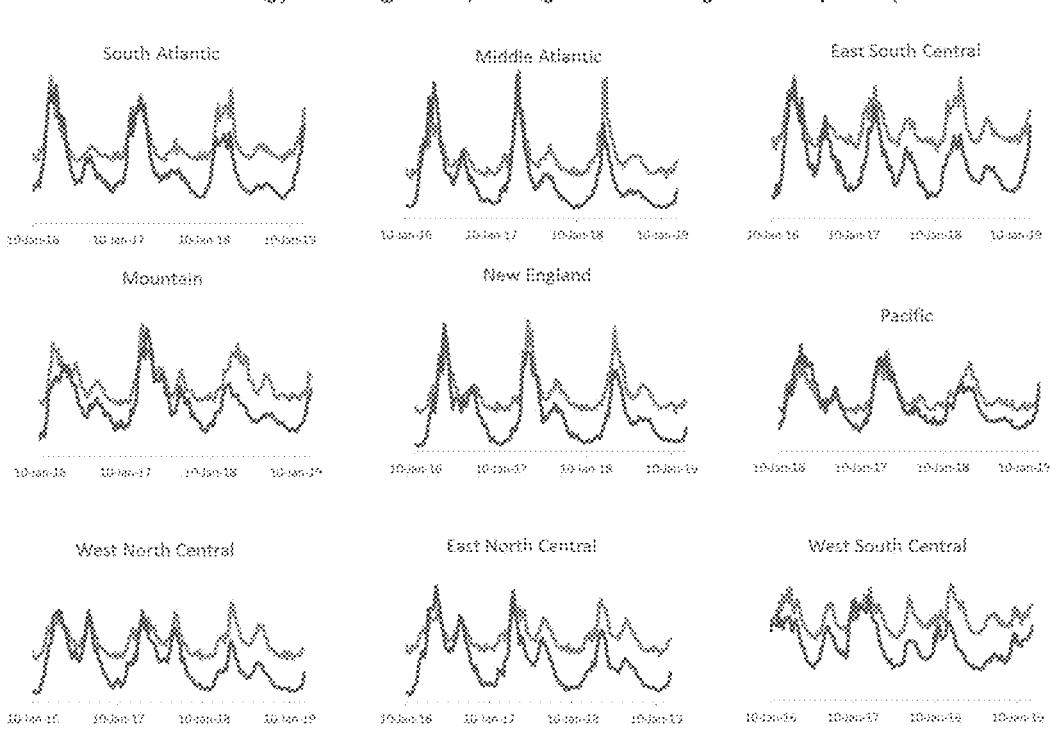

Figure 5:
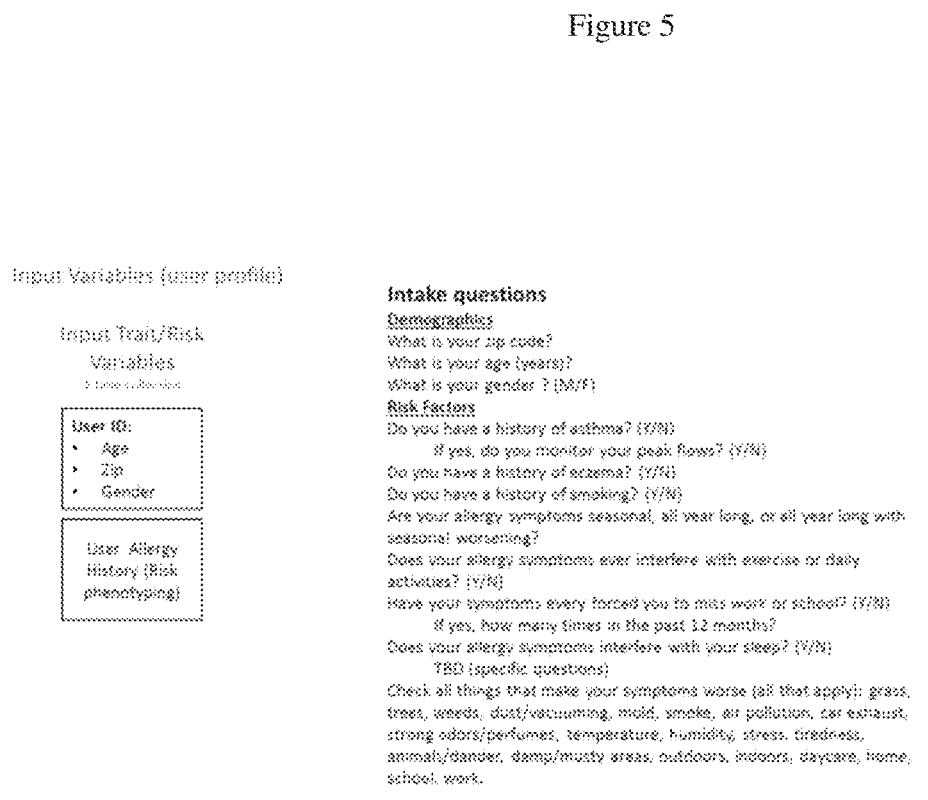

Input Variables (user profile)

Input Trait/Risk
Variables

User ID:
- Age
- Zip
- Gender

User Allergy
History (Risk
phenotyping)

Intake questions

__Demographics__
What is your zip code?
What is your age (years)?
What is your gender ? (M/F)

__Risk Factors__
Do you have a history of asthma? (Y/N)
    If yes, do you monitor your peak flows? (Y/N)
Do you have a history of eczema? (Y/N)
Do you have a history of smoking? (Y/N)
Are your allergy symptoms seasonal, all year long, or all year long with seasonal worsening?
Does your allergy symptoms ever interfere with exercise or daily activities? (Y/N)
Have your symptoms every forced you to miss work or school? (Y/N)
    If yes, how many times in the past 12 months?
Does your allergy symptoms interfere with your sleep? (Y/N)
    TBD (specific questions)
Check all things that make your symptoms worse (all that apply): grass, trees, weeds, dust/vacuuming, mold, smoke, air pollution, car exhaust, strong odors/perfumes, temperature, humidity, stress, tiredness, animals/dander, damp/musty areas, outdoors, indoors, daycare, home, school, work.

Figure 6

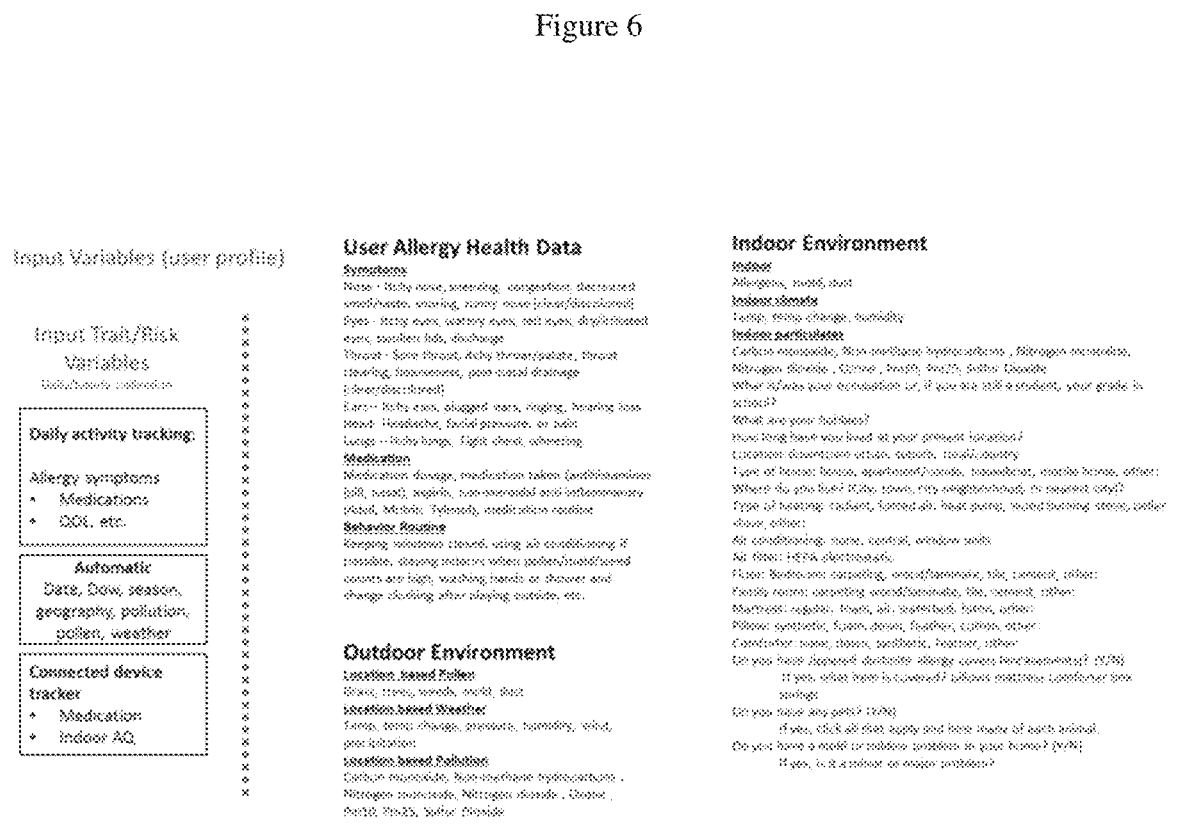

Input Variables (user profile)

Input Trait/Risk Variables

Daily activity tracking:

Allergy symptoms
* Medications
* OOL, etc.

Automatic
Date, Dow, season, geography, pollution, pollen, weather

Connected device tracker
* Medication
* Indoor AQ

User Allergy Health Data

Symptoms

Medication

Behavior Routine

Outdoor Environment

Location based Pollen

Location based Weather

Location based Pollution

Indoor Environment

Indoor

Indoor climate

Indoor particulates $S_nP_n/dt$ is the relationship between user symptoms ($S_n$) and allergens ($P_n$) over time (dt)

1) A method and framework to determine "My Allergy Impact"

Figure 9
2) A method and framework to forecast "My Allergy Impact"
My Predicted Allergy Impact (T1, T2, Etc.)
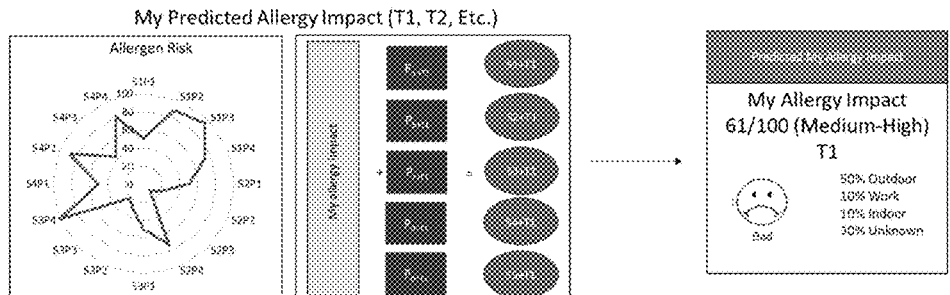
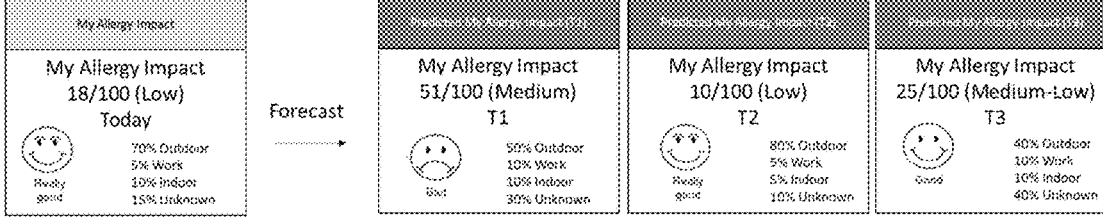

For each $S_n P_n$ calculate $Y (S_n \times dt) = X (P_n \times dt) \beta_i (\alpha_n \times dt) + \varepsilon$ My Allergy Impact = $\sum_{i=1}^{n}(SnPn) / \sum_{i=1}^{n}(ti)$ 3) A method and framework to recommend treatments based on "My Allergy Impact"

Segmenting "My Allergy Impact" with respect to treatments and behaviors

4) A method and framework to use "My Allergy Impact" as a digital liaison for OTC Rx Optimizing treatment regime through personalized data

METHOD TO MITIGATE ALLERGEN SYMPTOMS IN A PERSONALIZED AND HYPERLOCAL MANNER

The present application is a divisional of U.S. application Ser. No. 17/031,474 filed Sep. 24, 2020, which claims priority of the benefit of the filing of U.S. Provisional Application Ser. No. 62/904,834, filed Sep. 24, 2019, the contents of which are incorporated by reference herein in their entirety.

FIELD OF THE INVENTION

The present invention relates to a system and method for determining the potential impact of environmental conditions on an individual's allergy symptoms, and more particularly, to a system and method for predicting the impact that local environmental conditions may have on an individual's allergy symptoms in order to proactively treat the individual.

BACKGROUND OF THE INVENTION

Allergies occur when an individual's immune system reacts to a foreign substance. When exposed to a foreign substance such as pollen or pet dander, an individual's immune system produces substances known as antibodies. When an individual has allergies, his/her immune system makes antibodies that identify a particular allergen as harmful. When an individual comes into contact with the allergen, his/her immune system's reaction can inflame his/her skin, sinuses, airways and/or digestive system. Seasonal allergies are usually caused by plant pollen, which can come from trees, weeds and grasses in the spring, and by ragweed and other weeds in late summer and early fall. Hay fever, also called allergic rhinitis, can cause sneezing; itching of the nose, eyes or roof of the mouth; runny, stuffy nose; and watery, red or swollen eyes. Atopic dermatitis, an allergic skin condition also called eczema, can cause skin to itch; redden; flake or peel.

Allergic reactions can range from mild to severe. In some severe cases, allergies can trigger a life-threatening reaction known as anaphylaxis. Allergies can interfere with work, school or recreation. Allergies can also trigger or worsen asthma and lead to other health problems such as sinus and ear infections, particularly in children.

The severity of allergies varies from person to person. While most allergies can't be cured, treatments can help relieve allergy symptoms.

The U.S. Food and Drug Administration (FDA) regulates a number of medications that offer allergy relief.

Antihistamines reduce or block symptom-causing histamines and are available in many forms, including tablets and liquids. Many oral antihistamines are available over-the-counter and in generic form. Examples include Benadryl® (which contains the active diphenhydramine), Claritin® (which contains the active loratadine), Chlor-Trimeton® (which contains the active chlorpheniramine), and Zyrtec® (which contains the active cetirizine). Antihistamine nasal sprays are available by prescription only. An example includes NasalCrom® (which contains the active cromoglicic acid).

There are a number of formats of Zyrtec® product on the market, including, e.g., 24-hour tablets; 24-hour liquid gels; 24-hour dissolve tabs; 12-hour Zyrtec-D, which contains a combination of cetirizine and pseudoephedrine; 24-hour children's dissolve tabs, and 24-hour allergy syrup.

Nasal corticosteroids are typically sprayed into the nose once or twice a day to treat inflammation and reduce allergy symptoms. Nasal corticosteroids are available OTC and by prescription. An example includes Rhinocort® (which contains the active budesonide).

Decongestants are drugs available both by prescription and OTC and come in oral and nasal spray forms. Examples include Sudafed® (which contains the active pseudoephedrine) and Afrin® (which contains the active oxymetazoline). They are sometimes recommended in combination with antihistamines, which used alone do not have an effect on nasal congestion.

Immunotherapy is another option. One form of allergen immunotherapy is allergy shots in which an individual's body responds to injected amounts of a particular allergen, given in gradually increasing doses, by developing immunity or tolerance to that allergen.

Another form of allergen immunotherapy involves administering the allergens in a tablet form under the tongue (sublingual) and is intended for daily use, before and during the pollen season.

Seasonal allergic rhinitis (AR) is a common condition that causes symptoms such as sneezing, nasal congestion, runny nose, itchy nose or throat, watery eyes and itchy eyes. Most patients with AR report a wide range of practical problems resulting in a quality of life reduction.

Alleapp is an allergy tracking app with an Allergy SOS functionality for severe allergies that allows users to create their own network with family and friends for emergency contact. See https://theallergyapp.com.

myAllergyPal® by United Biologics, LLC dba United Allergy Services® is computer application software for mobile devices, namely, software for patients to access information related to and maintain compliance with allergy treatment. The developers indicate that this tool can be used to provide electronic message alerts via the internet notifying individuals of events, visits, appointments, and alerts relating to allergy treatment services. They also indicate that the technology enables users to manage treatment logs, communicate with professionals regarding health and wellness treatment, and maintain scheduling of allergy injections. The tool also includes a website featuring information about health and wellness, namely, allergens, allergies, and the remedies and treatments therefor. See https://apps.apple-.com/us/app/myallergypal/id1256088686.

Austin Allergy Tracker to Allergy & Asthma Associates PLLC samples pollen count and delivers an allergy report to the greater Austin area. The app, which provides an allergy report based on specific plants that trigger allergies, permits a user to track allergy symptoms. See https://apps.apple.com/us/app/austin-allergy-tracker/id1229265676.

The WebMD Allergy app helps a user control allergy symptoms by showing allergy levels in the user's area. See https://play.google.com/store/apps/details?id=com.webmd.allergy&hl=en_US.

U.S. Patent No. RE39,871 to AirAdvice, Inc. discloses an allergen/particulate data collection device and an air quality management device. See also https://www.airadviceforhomes.com/.

U.S. Published Application No. 20170038088 to Breezometer Ltd. discloses a system and method for generating air quality scores for air quality within certain locations. The method includes identifying at least one air pollution source within a predetermined perimeter around the at least one location; extracting an air quality score range based on the at least one location from at least one data source; identifying at least one environmental variable based on the at least one location and the at least one time parameter; simulating at least one air pollution measurement based on the at least one environmental variable and the at least one air pollution source; and generating at least one air quality score respective of the air quality score range, wherein the at least one air quality score is based on the at least one air pollution measurement. See also https://breezometer.com.

U.S. Published Application No. 20190156959 to Zambon SPA discloses a method for providing information indicative of concentration of at least one allergen in the environment that comprises: a) recording on a mobile device information relating to detection of a respiratory difficulty symptom in a person, wherein the recording comprises receiving from the person, via a graphical interface of the mobile device, at least one subjective information relating to the detected respiratory difficulty symptom and automatically generating at least one objective information relating to the detected respiratory difficulty symptom; b) sharing on a sharing server at least part of the information relating to the detected respiratory difficulty symptom and recorded on the mobile device; and c) at a further mobile device, receiving from the sharing server the shared at least part of the information relating to the detected respiratory difficulty symptom and displaying the shared at least part of the information relating to the detected respiratory difficulty symptom on a map shown by a display of the further mobile device. See also https://zambon.com/en.

WO2019102324 to MIR S.R.L.—Medical International Research discloses a system for monitoring the state of health of a patient suffering from a respiratory disease that includes a portable medical device having a flow measuring device capable of performing a spirometry measurement, and an oxygen measuring sensor capable of performing a measurement of blood oxygen saturation and heart rate.

U.S. Published Application No. 20190189258 to Reciprocal Labs Corporation d/b/a Propeller Health discloses a method for displaying patient information on a display of a computing device associated with a healthcare provider that includes patient asthma monitoring information for a set of asthma patients, the asthma monitoring for each patient including a report of rescue inhaler usage over a recent time window.

U.S. Pat. No. 10,255,412 to Reciprocal Labs Corporation discloses a method for measuring medicament device events that includes receiving a first medication usage event at a first time; analyzing the first event, the first time, and a medication dosage plan, the medication dosage plan specifying a dose time for a planned dose, a narrow time window comprising the dose time, and an expanded time window comprising the narrow time window and longer in duration than the narrow time window; and a second medication usage event at a second time later than the first time; and analyzing the first and second events, the first and second times, and the medication dosage plan to determine a dose characterization for the second event.

U.S. Published Application No. 20170109493 to Reciprocal Labs Corporation d/b/a Propeller Health discloses a method for providing chronic obstructive pulmonary disease (COPD) exacerbation risk notifications in real time that includes receiving, over a first time window, at least one historical COPD rescue medication event from a client computing device associated with the patient; storing the rescue medication events in a database in association with a patient profile; receiving, over a second time window occurring later in time than the first time window, at least one current COPD rescue medication event; and responsive to receiving the at least one current COPD rescue medication event, analyzing the historical COPD rescue medication events, and the at least one current COPD rescue medication event together to determine a risk of a COPD exacerbation for the patient; and sending a notification to the client computing device associated with the patient, the notification comprising the risk of the COPD exacerbation.

U.S. Pat. No. 10,726,954 to Reciprocal Labs Corporation d/b/a Propeller Health discloses an application server that employs trained models to predict respiratory disease risk, rescue medication usage, exacerbation, and healthcare. The reference discloses that the application server includes model modules and submodel modules, which communicate with a database server, data sources, and client devices. See also https://www.propellerhealth.com/how-it-works/.

U.S. Published Application No. 20160328537 to Johnson & Johnson Consumer Inc. discloses a system and method for verified reporting of illness states using disparate datasets. The reference discloses that the system and method receives multiple data feeds, collectively including illness report data from disparate data sources, and correlates disparate data sets from the disparate data sources to provide verified reporting of illness states. The reference also discloses that the verified reporting may be provided in the form of a geographical mapping of reported illness states displayed via a graphical user interface displayed by a computerized device, such that the mapping includes a visual indication of whether a mapped reporting from one data set is verified by being consistent with data from a disparate data set.

The cited references are incorporated by reference in their entirety herein.

Allergies are among the most common medical conditions worldwide and their prevalence continues to increase. Allergies have a high rate of misdiagnosis and therapeutic inefficacy. They often affect patients' quality of life and absorb health care resources.

Thus, there is a need for improved methods to treat allergy symptoms.

SUMMARY OF THE INVENTION

To help individuals with AR, the AllergyCast® App (see FIG. 1 (2009)) was developed to retrieve pollen and weather measurements specific to the individual's geographic location. Referring to FIG. 1, The App (a) provides a geographically based "Allergy Impact" score based on pollen count, weather, and social media; (b) provides a four day weather forecast; (c) tracks symptoms of the user by asking the user to describe how they feel on a zero to three scale, i.e., (1) "ugh"; (2) "meh"; (3) okay; and (4) great; and asks the user if they are experiencing symptoms, i.e., (1) sneezing; (2) nasal congestion; (3) watery eyes; (4) runny nose; (5) itchy eyes; and (6) itchy nose or throat; and (d) provides a monthly symptom tracker summary for the user. Over time, this tool is able to alert a user as to which pollens impact his/her well-being the most.

Leveraging the proprietary algorithm employed in the AllergyCast® App, the present inventors have developed a system and method to more specifically identify the impact of environmental conditions on allergic symptoms of an individual ("My Allergy Impact"), and tailor specific treatment recommendations in response to these environmental conditions and allergic symptoms.

By way of example, aspects of the present disclosure are directed to a system and method for determining the potential impact of environmental conditions on allergy symptoms of an individual. The system and method monitors environmental conditions of an individual and assists the individual with managing their allergy treatment in response to these environmental conditions and allergic symptoms.

The present invention provides a number of benefits, including:

personalized support;
    probabilistic assessment of success;
    targeted interventions;
    personalized content to address issues;
    access to expert advice; and
    optimized results.

DEFINITIONS

An "application programming interface" or "API" is a computing interface which defines interactions between multiple software intermediaries. It defines the kinds of calls or requests that can be made, how to make them, the data formats that should be used, the conventions to follow, etc.

"Classification analysis" is the supervised process of assigning items to categories/classes in order improve the accuracy of the analysis.

"Clustered data" arise when the data from a study can be classified into a number of different groups, referred to as clusters. Each cluster contains multiple observations, giving the data a "nested" or "hierarchical" structure, with individual observations nested within the cluster.

"Hyperlocal" is information oriented around a well-defined community with its primary focus directed toward the concerns of the population in that community.

"Linear regression" is a linear approach to modeling the relationship between a scalar response and one or more explanatory variables. The case of one explanatory variable is called simple linear regression. For more than one explanatory variable, the process is called multiple linear regression.

"Logistic regression" is a mathematical model used in statistics to estimate (guess) the probability of an event occurring having been given some previous data. Logistic regression works with binary data, where either the event happens (1) or the event does not happen (0).

A "longitudinal study" is a research design that involves repeated observations of the same variables over short or long periods of time.

"Machine learning models" are computer algorithms that improve automatically through experience. Examples include support vector models, k-nearest neighbors and random forests.

"Support-vector models" are supervised learning models with associated learning algorithms that analyze data used for classification and regression analysis.
    The "k-nearest neighbors" (KNN) algorithm is a simple, supervised machine learning algorithm that can be used to solve both classification and regression problems.
    "Random forests" are an ensemble learning method for classification, regression and other tasks that operate by constructing a multitude of decision trees at training time and outputting the class that is the mode of the classes or mean prediction of the individual trees.

"Multivariate regression" is a method used to measure the degree at which more than one independent variable (predictors) and more than one dependent variable (responses), are linearly related. The method is used to predict the behavior of the response variables associated to changes in the predictor variables, once a desired degree of relation has been established.

"My Allergy Impact" includes responding to an allergy symptom/treatment questionnaire as well as continued interaction with an allergy symptom/treatment tool.

"Negative binomial regression" is a type of generalized linear model in which the dependent variable is a count of the number of times an event occurs.

"Nested data" is individual data nested within data collected from multiple individuals in a group.

A "neural network" as used herein is an artificial neural network used for predictive modeling, adaptive control and applications where they can be trained via a dataset. Self-learning resulting from experience can occur within networks, which can derive conclusions from a complex and seemingly unrelated set of information.

"Pollen count" is an index of the amount of pollen particles in the air.

"Probabilistic approach" is employed when the designer no longer thinks of each variable as a probability distribution rather than a single number.

"Real time" as used herein is a process, action or transaction that involves updating information without artificial delay, i.e., at the same rate that the information is received.

"Regression" analysis is a set of statistical processes for estimating the relationships between a dependent variable and one or more independent variables.

Total Symptom Severity Complex" or "TSSC" is a prediction of an individual's allergy symptoms.

In accordance with an aspect of the invention, a system and method to determine the impact that environmental conditions may have on allergy symptoms of an individual to form an allergy impact profile for the individual, otherwise known as "My Allergy Impact", are provided.

In accordance with another aspect of the invention, a system and method to predict "My Allergy Impact" are provided.

In accordance with another aspect of the invention, a system and method to recommend treatments based on an individual's "My Allergy Impact" are provided.

In accordance with another aspect of the invention, a system and method to use an individual's "My Allergy Impact" as a digital liaison to determine appropriate treatment, including over-the-counter (OTC) and prescription (Rx) products and treatments, are provided.

By way of example, aspects of the present disclosure are directed to a system and method to create individualized allergy impact profiles. These individualized allergy impact profiles may be used to personalize treatment.

This SUMMARY is provided to briefly identify some aspects of the present disclosure that are further described below in the DETAILED DESCRIPTION. This SUMMARY is not intended to identify key or essential features of the present disclosure nor is it intended to limit the scope of any claims.

DESCRIPTION OF THE FIGURES

FIG. 1 shows the prior art Zyrtec® AllergyCast® App and pooled data from >250,000 users FIG. 2 shows the location methodology employed to determine an allergy impact profile in accordance with the invention.

FIG. 5 illustrates more specifically the types of questions that may be employed to gather static state variable information that is used to form an allergy impact profile in accordance with the invention.

FIG. 6 illustrates more specifically the types of questions that may be employed to gather dynamic variable information that is used to form an allergy impact profile in accordance with the invention.

FIG. 9 shows how an allergy impact profile can be forecasted and predicted 3-7 days in advance. Additionally, an overall summary month by month provides information as a it relates to the entire allergy season. This allows the user to understand their "My Allergy Impact" in a time dependent fashion (daily, weekly, and monthly, yearly).

DETAILED DESCRIPTION OF THE INVENTION

Definitions

According to an embodiment, the invention is directed to a system and method to determine an allergy impact profile.

Figure 2:
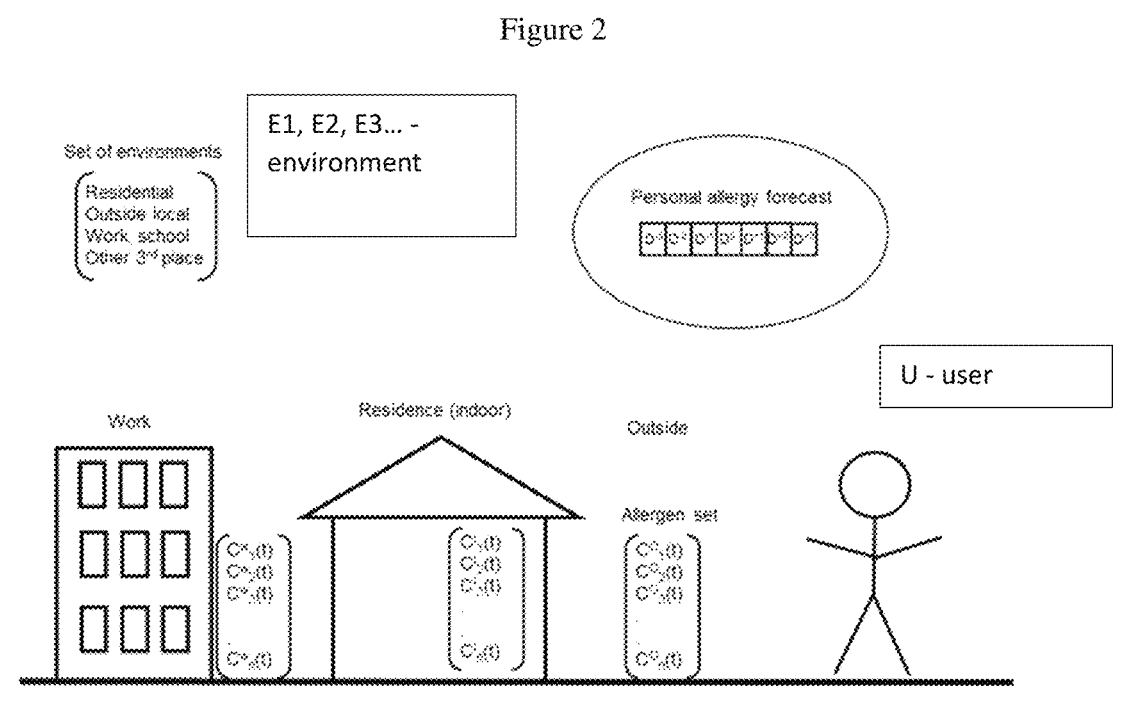

FIG. 2 shows the location methodology employed to determine an allergy impact profile in accordance with the invention. As shown in FIG. 2, a user, U, exposed to a set of environments, $E_1$, $E_2$, $E_3$ . . . . $E_n$, (e.g., residential, work, etc.) with a set of environmental conditions $C_1$, $C_2$, $C_3$ . . . . $C_n$, respectively, is provided with a personalized allergy impact profile otherwise known as "My Allergy Impact".

The invention thus includes a component for evaluating the needs of a user in real time and adjusting the "My Allergy Impact" when necessary. The invention incorporates evaluation of the user and correlates the evaluation with various inputs. The results of these analyses can be incorporated into rules operating on rules engine, which is included in software operating on a processing device, such as a mainframe computer, a desktop computer, a laptop computer, or a hand-held computational device such as a personal digital assistant or a cell phone. These rules may be stored in a data storage device, or alternatively, the rules may be generated real time during the environmental condition/allergy symptom.

Figure 3:
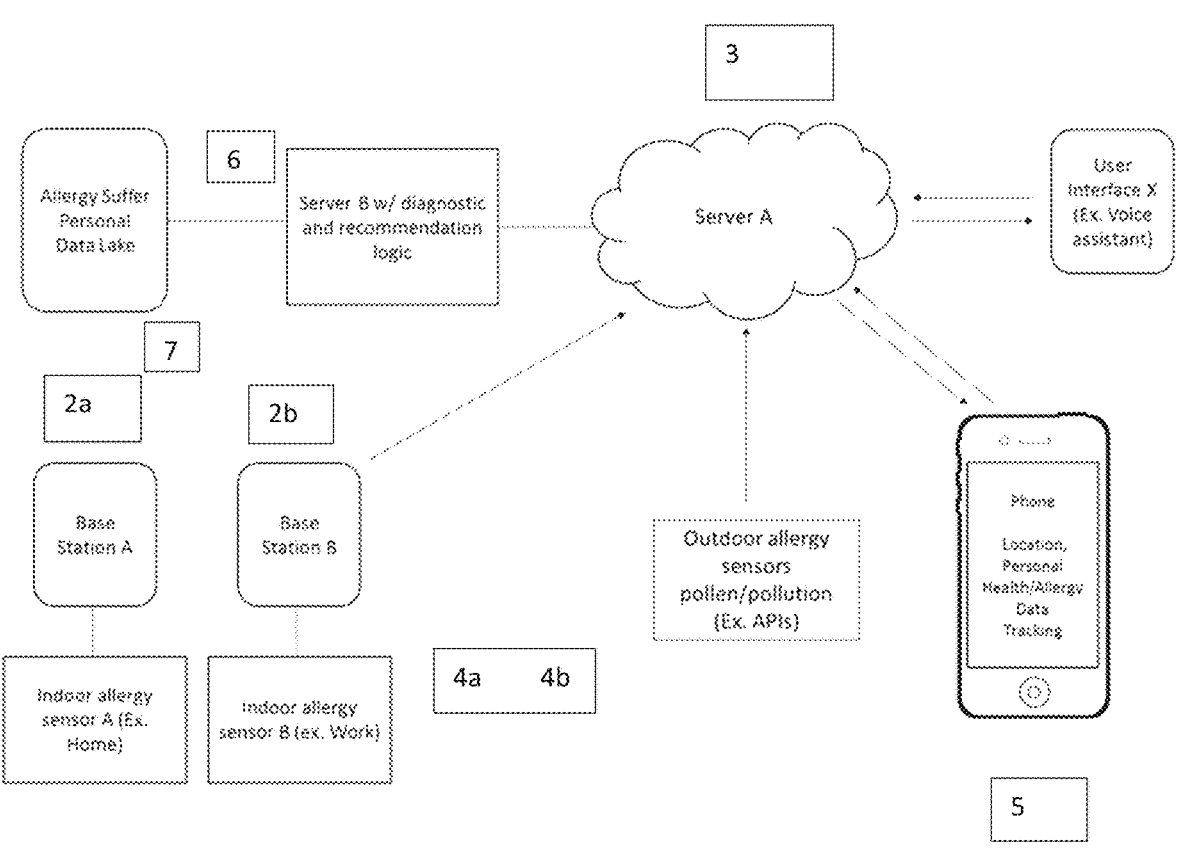
FIG. 3 shows the device and network methodology employed to predict an allergy impact profile in accordance with the invention.

FIG. 3 shows the device and network methodology employed to predict an allergy impact profile in accordance with the invention. According to aspects of the present disclosure, the system described herein preferably includes: a) base stations 2a and 2b in communication with a network 3, b) one or more sensors 4a and 4b in communication with the base stations 2a and 2b that are configured to monitor environmental conditions in proximity to the user, c) a communication device 5 in communication with the network 3; and d) a remote server 6 and associated data store 7 in communication with the network 3. The remote server 6 is operative to: 1) access information from the data store 7 indicative of information specific to the user, 2) receive information from the sensors 4a and 4b via the base stations 2a and 2b indicative of one or more measures of environmental conditions, 3) receive information from the communication device 5 indicative of user's location, 4) recommend at least one action to be taken as a function of the various inputs; and 5) transmit the recommended action to the communication device 5 for execution by the user.

According to another aspect of the present disclosure, the remote server 6 may thereafter be preferably operative to: a) confirm that the recommended action was applied, b) receive updated information from the sensors 4a and 4b indicative of environmental conditions, c) receive updated information from the communication device 5 indicative of location of the user, d) receive an updated user symptom; and e) evaluate the effectiveness of the recommended action in improving the user symptom.

Figure 4:
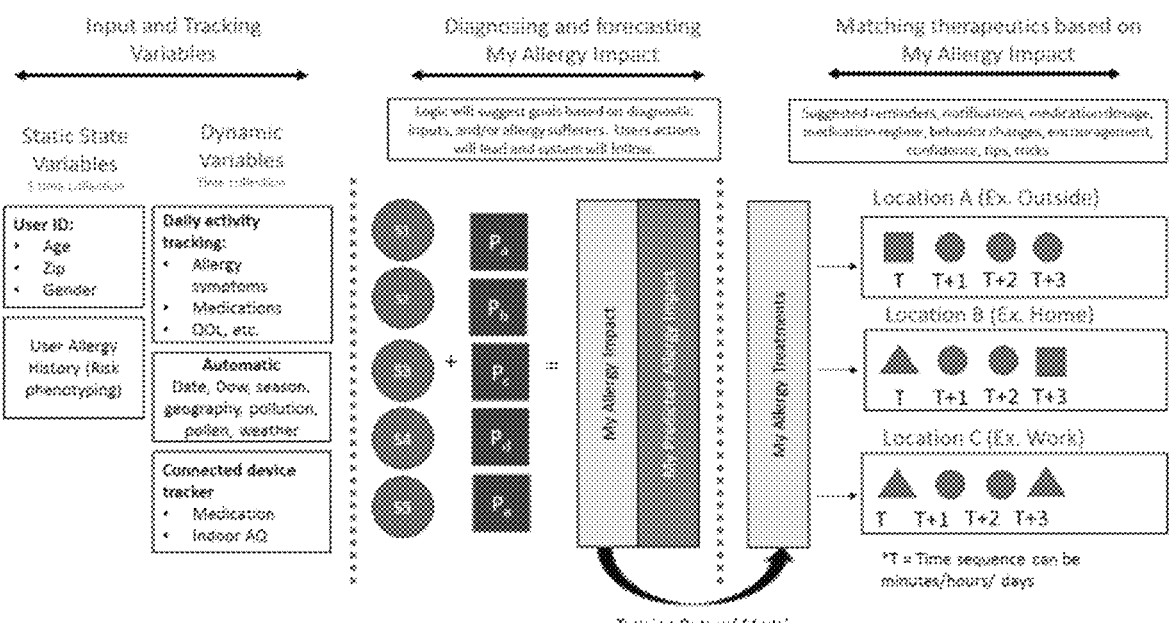
FIG. 4 shows the model framework employed to recommend treatment considering given allergy impact profile in accordance with the invention.

FIG. 4 illustrates an information flow for the remote server 6 (not shown) according to aspects of the present invention. The remote server 6 begins by establishing certain input and tracking variables that pertain to the user. For example, the remote server 6 may collect static state (i.e., one time collection) variable information to identify the user according to age, location (for example, zip code) and gender. The user may also be asked to provide an allergy history. This information may be referred to generally as identified input trait variables, which are static and require collection once or only infrequently. The remote server 6 may also collect dynamic (i.e., collection over time) variable information, such as (1) daily activity tracking of allergy symptoms, medications, quality of life (QOL); (2) automatic, e.g., date, day of week, season, geography, pollution, pollen, weather; and (3) connected device tracker, e.g., medication and indoor air quality. Using these inputs, decision logic, i.e., hypothesized descriptions of the chain of causes and effects leading to an outcome of interest in the form of "if-then" relationships between the various elements leading to the outcome, will diagnose and predict the user's allergy impact, otherwise referred to herein is "My Allergy Impact", and profile. Based on the user's "My Allergy Impact", the system may also suggest actions, goals, and/or treatments. The system can also match therapeutic treatment based on the user's "My Allergy Impact", e.g., medication, dose, behavior change, encouragement, confidence, etc. Specific treatment options are calculated using neural and probabilistic networks, which apply at least a portion of the large-scale data set crowdsourced information acquired according to the data assimilation. This portion of the data is used as training data for building best-fit models for minimizing specific allergy symptoms based on behavior or treatment option.

FIG. 5 illustrates more specifically the types of questions that may be employed to gather static state variable information.

FIG. 6 illustrates more specifically the types of questions that may be employed to gather dynamic variable information.

Figure 7:
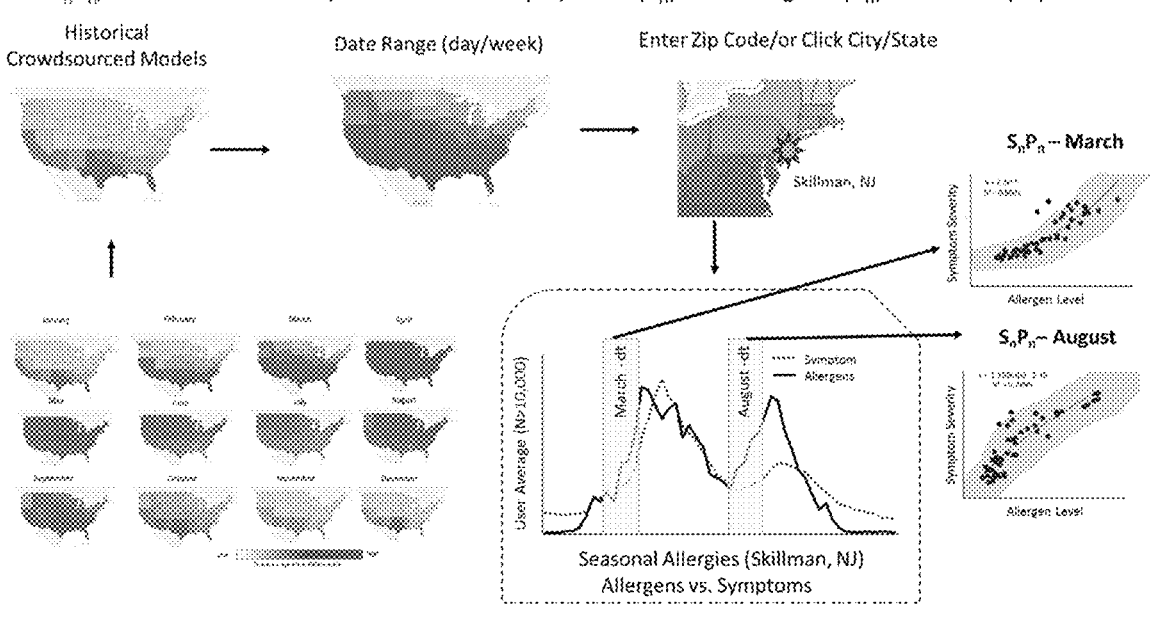
FIG. 7 illustrates that the relationship between an individual's allergy symptoms and outdoor allergens is hyper-local.

FIG. 7 illustrates that the relationship between a user and outdoor allergens are hyperlocal and directly measurable.

Figure 8:
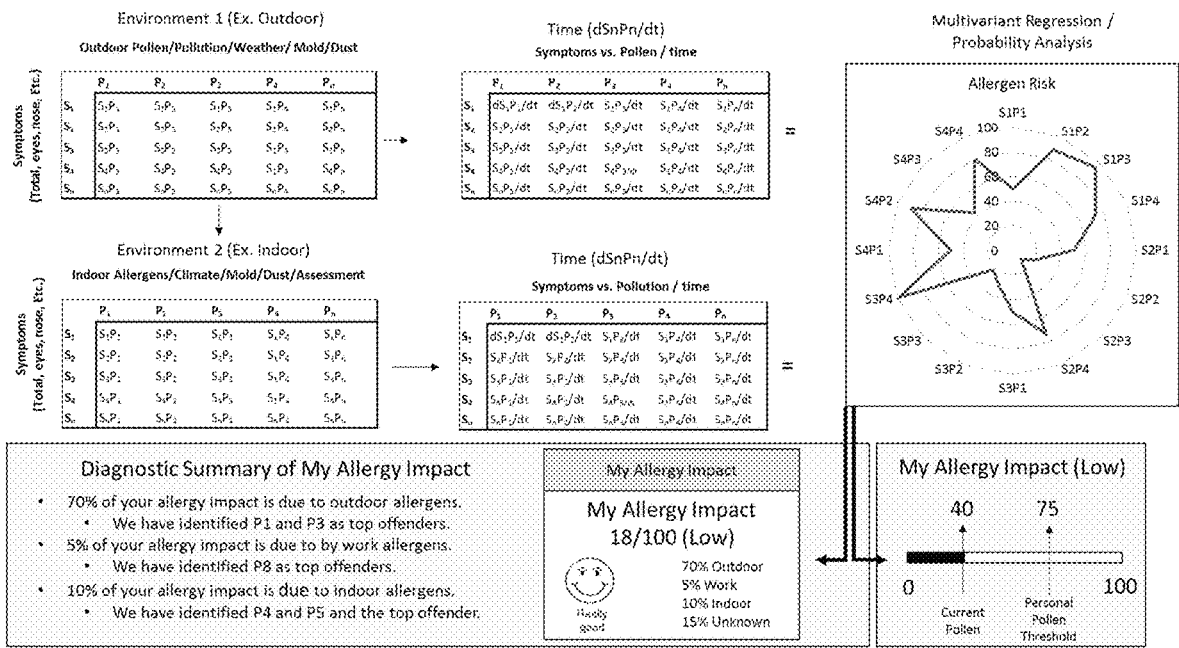
FIG. 8 shows the methodology employed to combine multiple environmental allergens and conditions and symptoms into a composite "My Allergy Impact" profile in accordance with the invention.

FIG. 8 shows the methodology employed to combine multiple environmental allergens and conditions and symptoms into a composite "My Allergy Impact" profile in accordance with the invention. Using direct and indirect information from a user taken over time, this method involves the combination of multiple inputs into a composite profile. The mere fact that a user opens the App is an indication that the user is experiencing allergy symptoms. Therefore, each time the user uses the App is one of the factors considered in the method of the invention.

FIG. 9 shows how the "My Allergy Impact" profile can be forecasted and predicted 3-7 days in advance. Additionally, an overall summary month by month provides information as a it relates to the entire allergy season. This allows the user to understand their "My Allergy Impact" in a time dependent fashion (daily, weekly, and monthly, yearly).

Figure 10:
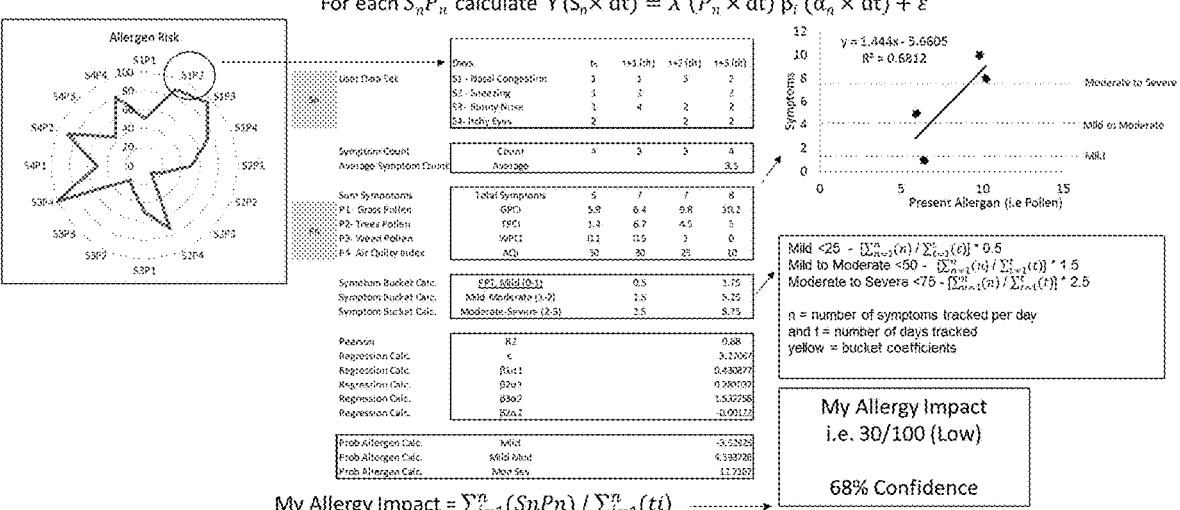
FIG. 10 shows an example of a calculation employed to determine a "My Allergy Impact" profile in accordance with the invention.

FIG. 10 shows an example of a calculation employed to determine an allergy impact profile in accordance with the invention. User tracking data is inherently a longitudinal study, wherein an outcome is measured for the same individual at multiple time points (repeated measures), or the modeling of nested/clustered data, wherein there are multiple individuals in each cluster. $S_nP_n/dt$=change in symptom and allergen relationship over time. Using a multivariate regression or probabilistic approach, data is modeled using longitudinal studies, wherein an outcome is measured for the same individual at multiple time points (repeated measures), or the modeling of nested/clustered data, wherein there are multiple individuals in each cluster. Y $(Sn \times dt)$=X(Pn\times dt) $\beta n(\alpha i \times dt)$+$\epsilon$, where Y equals dependent variables, X equals predictor variables, S equals specific symptoms, P equals specific allergens, n equals number of variables, $\beta$ equals allergen coefficients, $\alpha i$ equals time dependent coefficients dt equals time change, and $\epsilon$ equals intercept.

The personalized symptom prediction technology calculates how an individual may feel any given day. When an individual first starts using the app, he/she is provided with environmental conditions data, including, e.g., the pollen count in his/her area. The user can then track symptoms and other user specific information in the app for a period of time, after which personalized predictions can be provided. Symptom severity can be calculated using unique-to-user factors like environmental conditions; tracked symptoms data; and, as discussed below, data of users similarly situated to the user.

My Allergy Impact Ratings can be assigned on a rating basis of any scale, e.g., 0-10; 0-12; 0-100. A preferred rating basis is on a scale of 0-12, wherein low impact rating is from 0<=3; mild impact rating is from 3<=6; moderate impact rating is from 6<=9; and severe impact rating is from 9<=12.

The user's results can be used to recommend courses of action in real time or the user can share results with his/her physician, who can recommend courses of action.

Individual level allergy symptom level predictions can be made using personal, individual data (as shown previously). This data can include environmental factors (e.g., pollen, weather, pollution), as well as factors specific to an individual's behavior (e.g., treatment regimes, compliance/adherence to a product, symptom perception).

Additionally, as discussed above, predictions can be made using population level data to help augment the prediction for a particular user with significantly more data. An ensemble approach that pools data similar to a particular user (e.g., within the same zip code, township, city, state or other regional basis) is created to grab users with similar environmental conditions (e.g., pollen, pollution, weather). A model can then be trained on the population level data. This has significant advantages due to larger volume of data. For example, a zip code may have between 50-100 AllergyCast® users who have recently submitted data, and this larger volume of data enables the use of more classical machine learning models (e.g., support vector machines, k-nearest neighbors, random forests) with less risk of bias due to small datasets.

Population level models can be created using known geographical data (e.g., zip code, township, city, state or other regional basis) or using a clustering algorithm to create clustering constructs. For example, the data could be clustered using an unsupervised machine learning algorithm, e.g., k-means, which can propose an optimum number of clusters and grouping of individuals. This approach allows the testing of less arbitrary grouping schemas (e.g., zip codes, which have no inherent meaning to the data).

Population level models can also be combined in a voting scheme to help contribute towards an individual's overall prediction. For example, suppose that the model consists of three main tiers:

1. Individual model: trained solely on an individual's data;

2. City model: trained on all data collected at the individual's zip code;

3. State model: trained on all data collected at the individual's state.

After all three models are trained, they can be fed input data from the user. Each model can then use this data and predict the user's symptom level. This approach has the advantage of leveraging larger volumes of data by listening to population level trends.

The previous schema can be altered using different groupings of consumers (e.g., algorithmic clustering like through k-means) and a weighting schema can be used to bias the vote (e.g., for a particular user, the population data may have more of an impact and its vote can be weighted higher).

Accuracy

As seen in the table below, the present inventors determined that there was a poor relationship between pollen count and a user's overall allergy symptoms. In accordance with the invention, how key symptoms contribute to a user's overall symptoms are employed along with environmental conditions such as pollen count to obtain a more personalized score for the user.

The present inventors also determined that there was a strong correlation between app usage and treatment compliance.

As can be seen in the table below, the invention exhibits improved accuracy in predicting allergy severity of its users over tracking environmental pollen count alone.

| Model | Parameters | Rating | Algorithm accuracy for detecting allergy severity |
|---|---|---|---|
| Linear regression | Pollen score, TSSC | Allergy score (0-12), Allergy category (low, mild, moderate, severe) based on predefined interval | 38.9% |
| Logistic regression | Pollen score, overall symptoms | Allergy category (low, mild, moderate, severe) | 73.4% |
| Hybrid; multi-variate and linear regression | key symptoms, Pollen score (8 variables) | Personal TSSC (0-21), Allergy score (0-12), Allergy category (low, mild, moderate, severe) based on predefined interval | 63.9% |

Hybrid Regression Model

Figure 16:
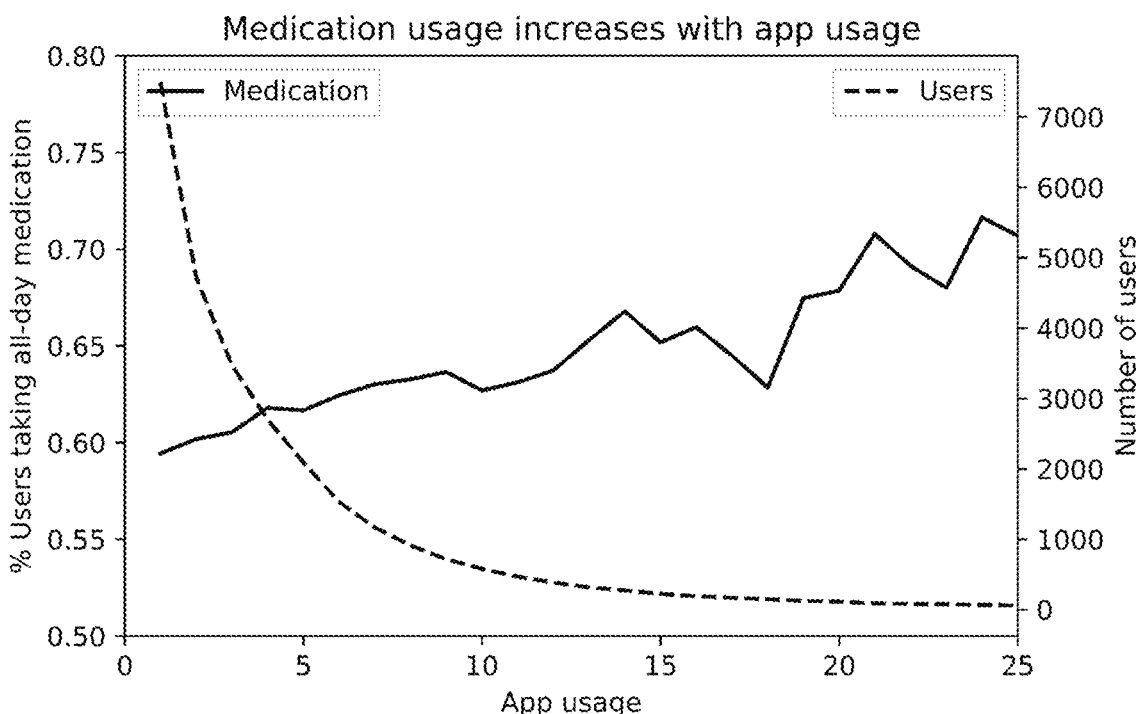
FIG. 16 is a graphical representation that demonstrates that medication usage increases with app usage.
Figure 17:
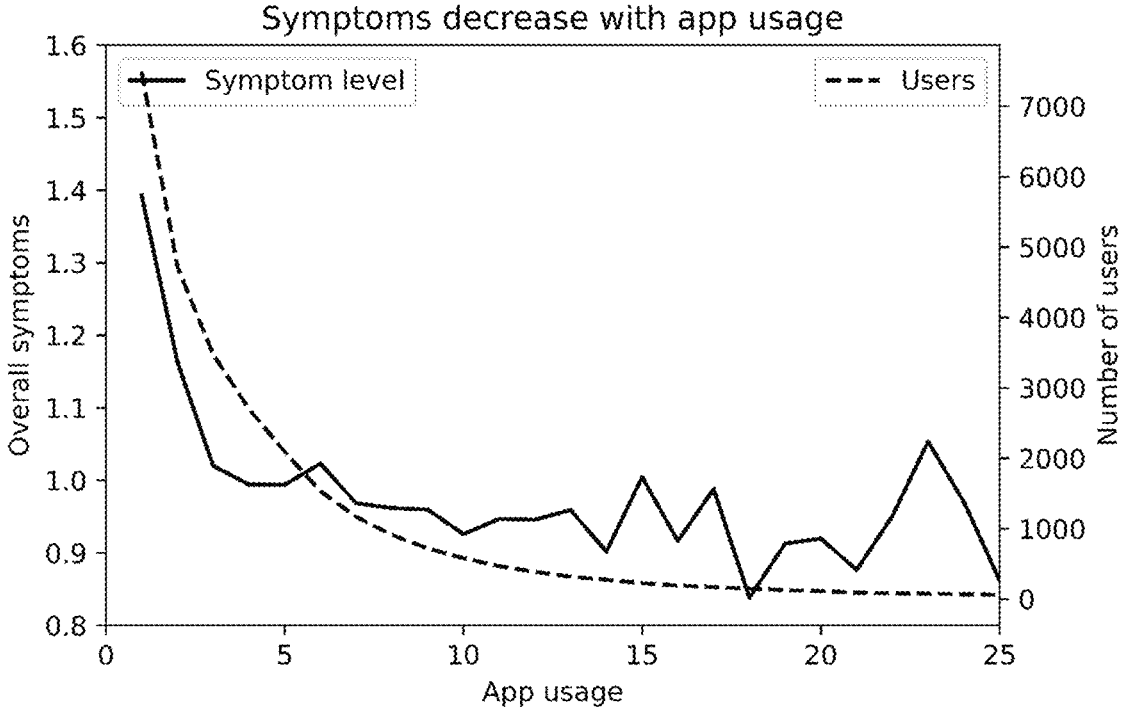
FIG. 17 is a graphical representation that demonstrates that symptoms decrease with app usage.

Multivariate regression model to estimate individual TSSC based on severity of his/her key symptoms Linear regression model to estimate individual TSSC based on environmental pollen count Treatment Compliance Two months of data shows that among users who use the app to track their allergy symptoms each day consecutively for seven days 70% of them use a 24-hour allergy medication at least once in those seven days; and that 64% of those who used a 24-hour allergy medication used it consistently each day of those seven days. See FIG. 16. The data also show that symptoms decrease with increasing days of app usage. See FIG. 17. This suggests that the app can assist users with compliance of allergy treatment regimens.

Figure 11:
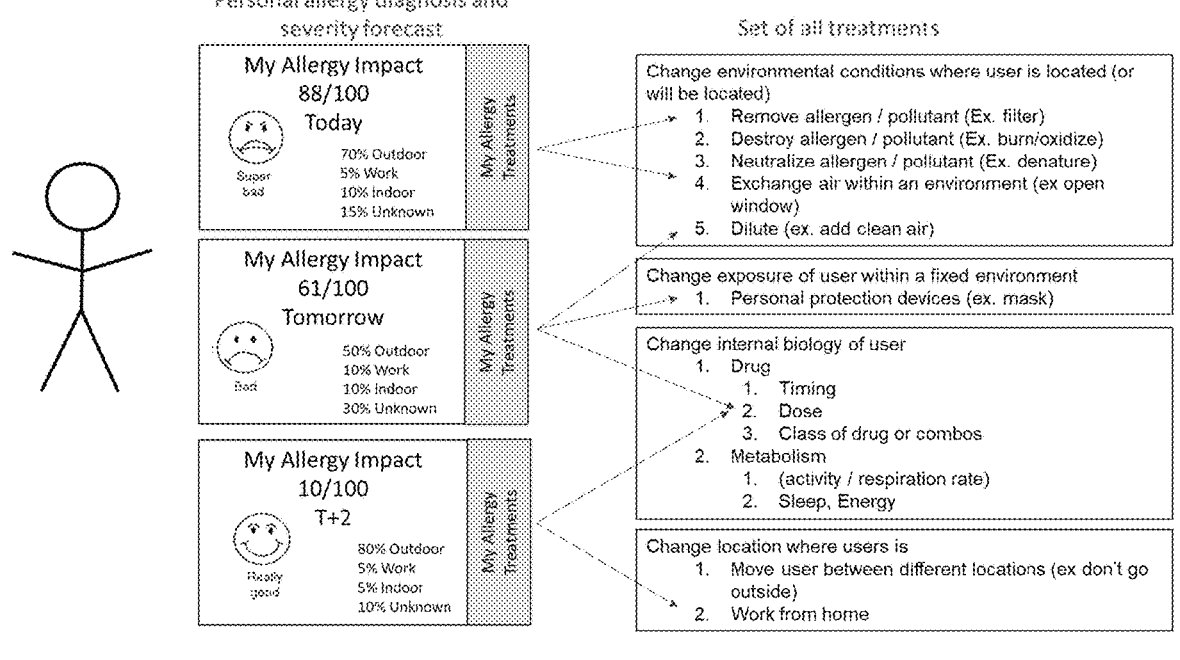
FIG. 11 shows examples of potential treatments in response to an individual's "My Allergy Impact" profile determined in accordance with the invention.

FIG. 11 shows examples of potential treatments in response to an individual's allergy impact profile determined in accordance with the invention. Such treatments include, e.g., 1) change environmental conditions where user is located, 2) change exposure of user within fixed environment, 3) change internal biology of user, 4) change location where user is; 5) and recommend medication, including OTC medication such as Zyrtec® 24-hour tablets; Zyrtec® 24-hour liquid gels; Zyrtec® 24-hour dissolve tabs; Zyrtec®24-hour children's dissolve tabs, and Zyrtec®24-hour allergy syrup. Depending on the symptoms and their severity, the OTC medication can be, e.g., 12-hour Zyrtec-D, which contains a combination of cetirizine and pseudoephedrine.

Specific examples can be shown and compliance can be tracked within the mobile app.

Figure 12:
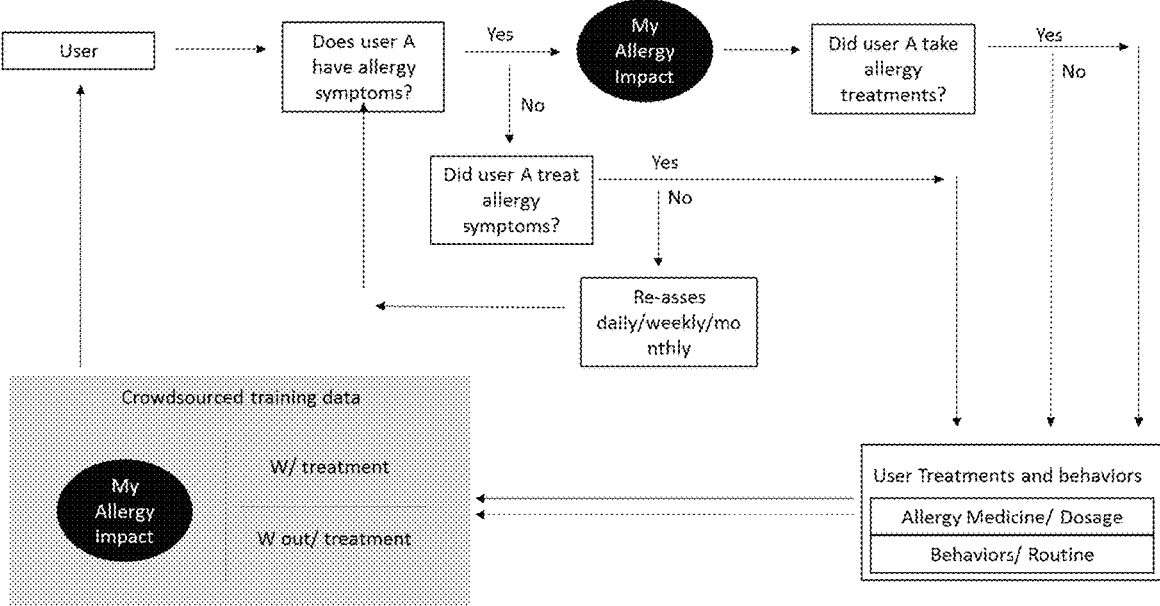
FIG. 12 shows how "My Allergy Impact" profile can be segmented by either medication/behavior response or no response.

FIG. 12 shows how "My Allergy Impact" profile can be segmented by either medication/behavior response or no response. If a user is experiencing symptoms, "My Allergy Impact" can be calculated. Based on the tracked treatment data, "My Allergy Impact" can either be calculated without treatment (control) or with treatment. This difference (response-control) provides comparison data set used to calculate efficacy of treatment options.

Figure 13:
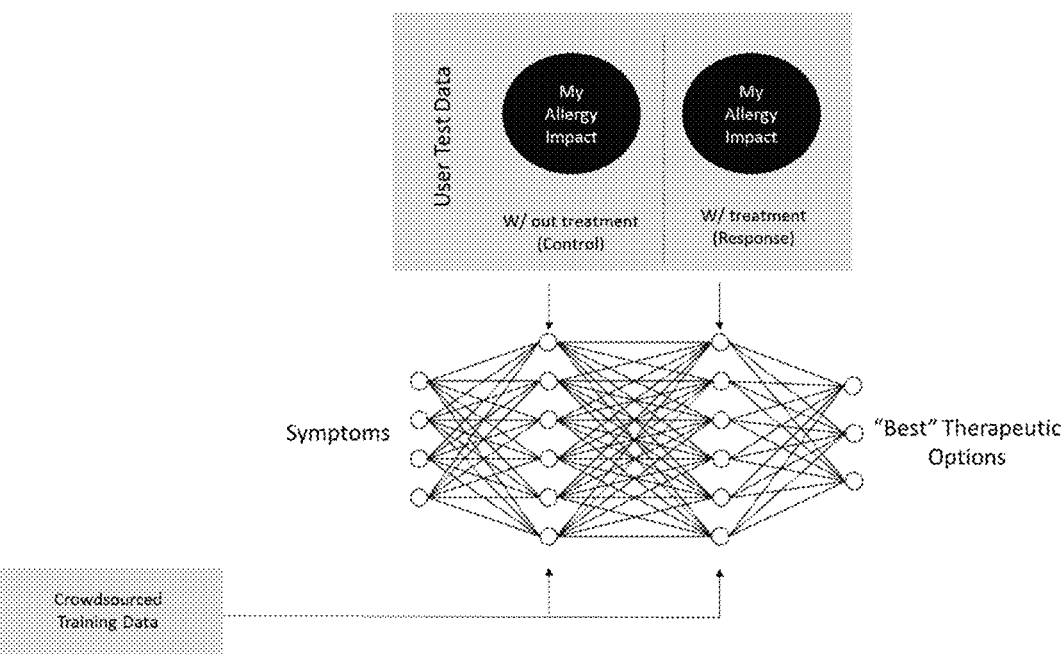
FIG. 13 shows how modeling through neural nets (in combination with "My Allergy Impact" profile) can be employed to determine the best treatment for given environmental condition and symptoms.

FIG. 13 shows how modeling through neural nets (in combination with "My Allergy Impact" profile) can be employed to determine the best treatment for given environmental condition/symptom. Specifically, FIG. 13 depicts an analysis engine for analyzing data described in reference to FIG. 11 and FIG. 12 and provides actions for changing behaviors or treatments. The engine is preferably implemented as a neural network, which applies at least a portion of the large-scale data set crowdsourced information acquired according to the data assimilation hierarchy in FIG.

7 and FIG. 8. This portion of the data is used as training data for building best-fit models for minimizing specific allergy symptoms based on behavior or treatment options.

Figure 14:
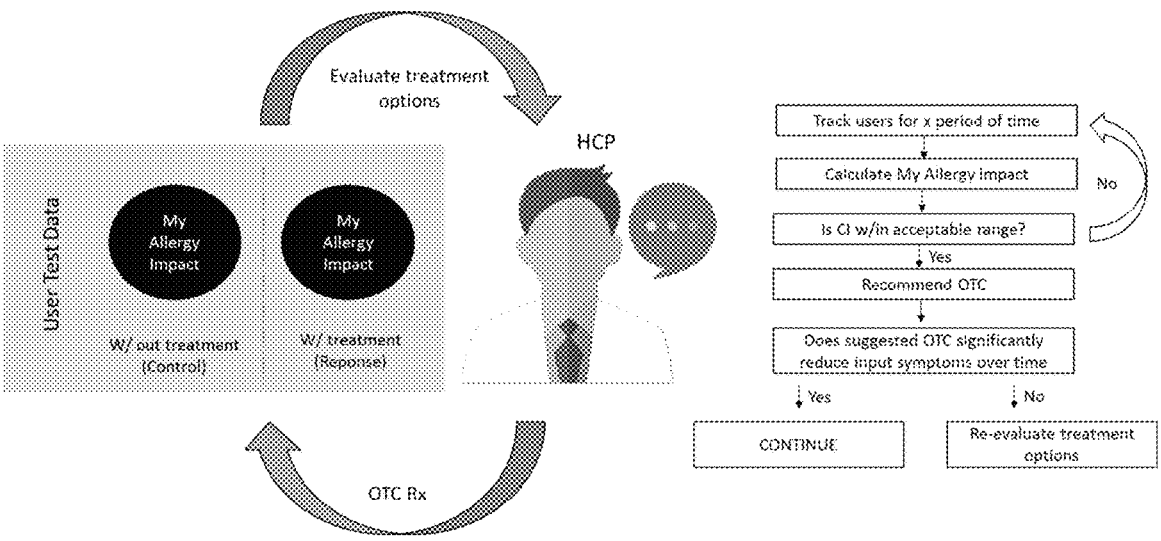
FIG. 14 shows how "My Allergy Impact" profile and best treatment for given environmental condition/symptoms can be used by doctors to prescribe OTC allergy medications.

FIG. 14 shows how "My Allergy Impact" profile and best treatment for given environmental condition/symptoms can be used by doctors to recommend OTC and/or prescribe Rx allergy medications. Doctors will observe "My Allergy Impact" profile with and without treatments and evaluate confidence interval. If there is good consensus that symptoms are due to indoor/outdoor allergens, OTC medications can be recommended and/or Rx medications can be prescribed.

Figure 15:
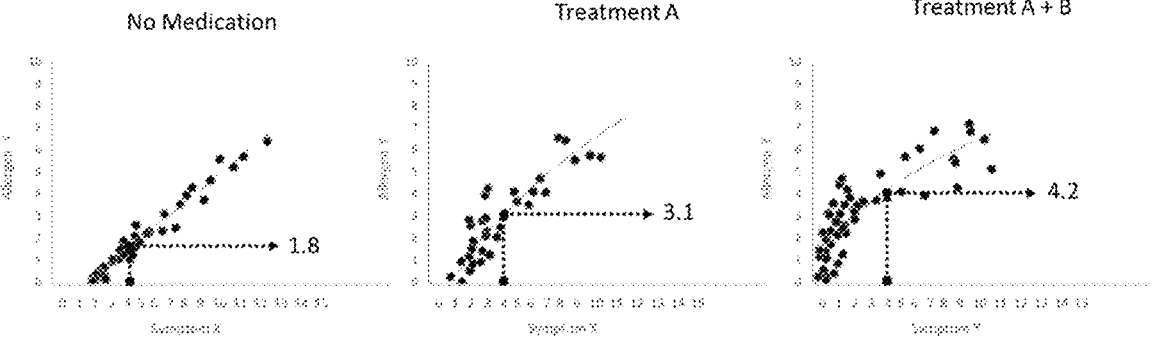
FIG. 15 shows how the combination of treatments based on "My Allergy Impact" can be employed to determine the best therapeutic for given environmental condition/symptoms.

FIG. 15 shows how the combination of treatments can be employed to minimize "My Allergy Impact" and determine the best therapeutic for given environmental condition/symptom. For example, with no treatments a pollen threshold may be at 1.8 (High). However upon one treatment, pollen thresholds may increase to 3.1 (Medium High) and with two treatments, pollen thresholds may increase to 4.2 (Medium).

Thus, the invention is also to a system and method that can be used to match a user's allergy impact, otherwise referred to herein as "My Allergy Impact", profile with a recommended treatment. In essence, this aspect of the invention relates to a quantitative multi-dimensional means to individualize and optimize treatment.

It will be understood that, while various aspects of the present disclosure have been illustrated and described by way of example, the invention claimed herein is not limited thereto, but may be otherwise variously embodied according to the scope of the claims presented in this and/or any derivative patent application.

The invention claimed is:

1. A system directed to monitor the impact that environmental conditions may have on a user, the system comprising:

a plurality of base stations in communication with a network comprising a remote server in communication with the network;

a plurality of indoor and outdoor sensors in communication with the base stations, the sensors configured to monitor environmental conditions in proximity to the user; and a communication device including an app in communication with the network;

wherein the remote server includes a computerized processing device and is operative to:

access stored information indicating one or more user information, wherein the user information is selected from the group consisting of age, location, daily activity tracking of allergy symptoms, medications, quality of life (QOL), date, day of week, season, geography, pollution, pollen, weather, medication, treatment regime (including medication response, or no response, data), and indoor air quality;

receive information from the sensors via the base stations indicative of one or more measures of environmental conditions, receive information from the communication device indicative of the user information measuring an outcome of the user's information, the measuring comprising:

calculating, for the user, on the computerized processing device, the change in symptom and allergen outcome relationship over time (SnPn/dt) (or the modeling of nested/clustered data, wherein there are multiple individuals in each cluster) using a multivariate regression or probabilistic approach;

generating and including on the computerized processing device an analysis engine for analyzing potential treatment options based on the user's information regarding the user's response (or no response) to medication in combination with the calculated change in symptom and allergen outcome relationship over time (SnPn/dt) data by i) using for each SnPn, Y (Sn×dt)=X (Pn×dt) $\beta$n ($\alpha$i×dt)+$\epsilon$, where Y equals dependent variables, X equals predictor variables, S equals specific symptoms, P equals specific allergens, n equals number of variables, $\beta$ equals allergen coefficients, $\alpha$i equals time dependent coefficients dt equals time change, and $\epsilon$ equals intercept and ii) applying at least a portion of the crowdsourced information acquired from the SnPn/dt relationship between user symptoms (Sn) and allergens (P) over time (dt) and the user's information tracked over time;

employing the analysis engine to train machine learning models for increasing the user's pollen threshold, wherein the machine learning models are selected from support vector machines, k-nearest neighbors, random forests or mixtures thereof, wherein training comprises generating a tiered ensemble of the machine learning models using pooled data from users having environmental conditions similar to those of the target user, wherein the tiered machine learning models are each configured to receive target user input data and output a symptom level, and said outputs are combined using a weighted voting scheme to produce an overall prediction, where the voting weights are based on relative data impact; and comparing factors specific to said user's behavior to the machine learning models, using the computerized processing device, to determine one or more treatment recommendation(s) for increasing the user's pollen threshold;

wherein the system recommends at least one allergy treatment intervention in real time;

wherein the system transmits the recommended allergy treatment intervention to the communication device; and wherein the communication device provides in the app a personalized allergy impact profile for the user and the recommended allergy treatment for the user.

\* \* \* \* \*